United States Patent
Loesch et al.

(10) Patent No.: US 8,529,805 B2
(45) Date of Patent: Sep. 10, 2013

(54) METHOD FOR THE PRODUCTION OF WATER ABSORBENT POLYMER PARTICLES BY POLYMERIZING DROPS OF A MONOMER SOLUTION

(75) Inventors: Dennis Loesch, Altrip (DE); Matthias Weismantel, Jossgrund-Oberndorf (DE); Marco Krüger, Mannheim (DE); Antje Ziemer, Mannheim (DE)

(73) Assignee: BASF SE, Ludwigshafen (DE)

( * ) Notice: Subject to any disclaimer, the term of this patent is extended or adjusted under 35 U.S.C. 154(b) by 294 days.

(21) Appl. No.: 12/438,226

(22) PCT Filed: Oct. 2, 2007

(86) PCT No.: PCT/EP2007/060416
§ 371 (c)(1),
(2), (4) Date: Feb. 20, 2009

(87) PCT Pub. No.: WO2008/040714
PCT Pub. Date: Apr. 10, 2008

(65) Prior Publication Data
US 2009/0192036 A1    Jul. 30, 2009

(30) Foreign Application Priority Data
Oct. 5, 2006 (EP) ..................... 06121838

(51) Int. Cl.
*B29B 9/00* (2006.01)
*A61J 3/07* (2006.01)
*B29C 39/10* (2006.01)

(52) U.S. Cl.
USPC ........ 264/13; 264/4; 264/7; 264/14; 604/372; 428/402.24

(58) Field of Classification Search
USPC ............. 525/78; 428/402, 402.22; 239/423, 239/424; 264/4
See application file for complete search history.

(56) References Cited

U.S. PATENT DOCUMENTS

| | | | | |
|---|---|---|---|---|
| 4,873,299 A | * | 10/1989 | Nowakowsky et al. | 526/73 |
| 4,997,867 A | * | 3/1991 | Jederstrom et al. | 524/47 |
| 5,269,980 A | | 12/1993 | Levendis et al. | |
| 5,888,538 A | * | 3/1999 | Kiefer et al. | 424/451 |
| 6,174,952 B1 | * | 1/2001 | Hekal et al. | 524/503 |
| 6,780,507 B2 | * | 8/2004 | Toreki et al. | 428/402.21 |
| 7,914,714 B2 | * | 3/2011 | Anchordoquy et al. | 264/4.1 |
| 2002/0146386 A1 | * | 10/2002 | Simon et al. | 424/78.31 |
| 2004/0012105 A1 | * | 1/2004 | Deppe et al. | 264/4 |
| 2004/0131855 A1 | * | 7/2004 | Ganapathiappan | 428/407 |
| 2006/0217508 A1 | | 9/2006 | Schmid et al. | |
| 2007/0100115 A1 | | 5/2007 | Schmid et al. | |
| 2007/0244280 A1 | | 10/2007 | Losch et al. | |
| 2007/0264489 A1 | * | 11/2007 | Sasabe et al. | 428/327 |
| 2008/0045624 A1 | | 2/2008 | Losch et al. | |
| 2008/0045625 A1 | | 2/2008 | Losch et al. | |
| 2008/0125533 A1 | | 5/2008 | Riegel et al. | |
| 2008/0188586 A1 | * | 8/2008 | Bruhns et al. | 522/153 |
| 2008/0188821 A1 | * | 8/2008 | Losch et al. | 604/372 |
| 2008/0194778 A1 | | 8/2008 | Losch et al. | |

FOREIGN PATENT DOCUMENTS

| | | |
|---|---|---|
| DE | 103 14 466 | 10/2004 |
| DE | 103 40 253 | 3/2005 |
| DE | 10 2004 024 437 | 12/2005 |
| DE | 10 2004 042 946 | 3/2006 |
| DE | 10 2004 042 948 | 3/2006 |
| DE | 10 2004 042 955 | 3/2006 |
| DE | 10 2005 019 398 | 10/2006 |
| EP | 348 180 | 12/1989 |
| EP | 1 424 346 | 6/2004 |
| EP | 1424346 * | 6/2004 |
| JP | 05132503 A | 5/1993 |
| WO | WO-96/40427 | 12/1996 |
| WO | WO-2006/042704 | 4/2006 |
| WO | WO-2006/077054 | 7/2006 |
| WO | WO-2006/120232 | 11/2006 |

OTHER PUBLICATIONS

Buchholz et al., *Modern Superabsorbent Polymer Technology*, Wiley-VCH, pp. 71-103 (1998).
Deutsche Anmeldung Aktz. 10 2006 001 596.7.

* cited by examiner

*Primary Examiner* — Irina Krylova
(74) *Attorney, Agent, or Firm* — Marshall, Gerstein & Borun LLP

(57) ABSTRACT

The invention relates to a method for the production of water absorbent polymer particles by polymerizing drops, comprising at least one monomer in a gas phase surrounding the drops, wherein the drops are produced by surrounding a first monomer solution with a second monomer solution and polymerizing the second monomer solution to a higher crosslinked polymer than the first monomer solution.

8 Claims, 1 Drawing Sheet

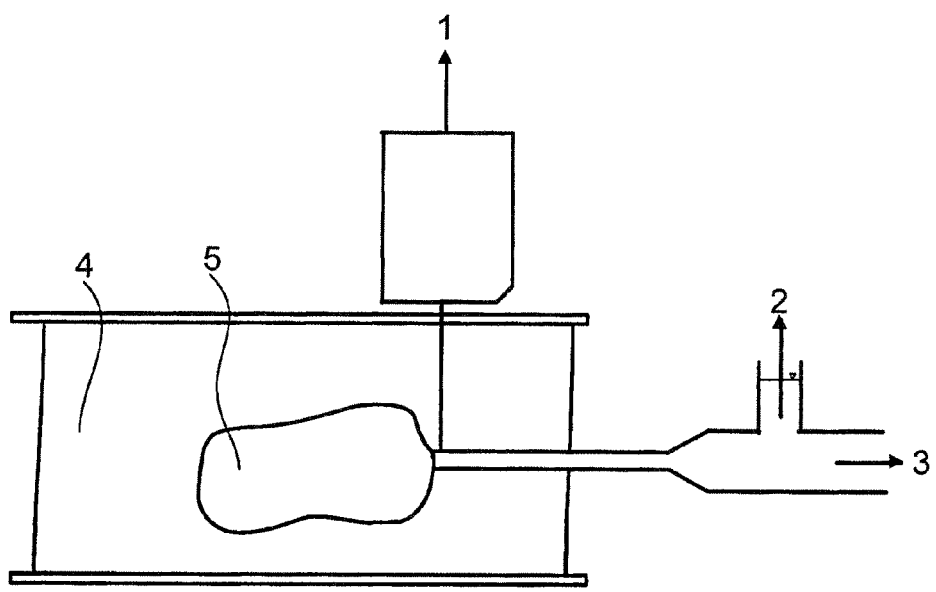

METHOD FOR THE PRODUCTION OF WATER ABSORBENT POLYMER PARTICLES BY POLYMERIZING DROPS OF A MONOMER SOLUTION

CROSS-REDERENCE TO RELATED APPLICATIONS

This is the U.S. national phase of International Application No. PCT/EP2007/060416, filed Oct. 2, 2007, which claims the benefit of European Patent Application No. 06121838.4, filed Oct. 5, 2006.

DESCRIPTION

The present invention relates to a process for preparing water-absorbing polymer beads by polymerizing droplets comprising at least one monomer in a gas phase surrounding the droplets, the droplets being obtained by surrounding a first monomer solution with a second monomer solution and polymerizing the second monomer solution to give a more highly crosslinked polymer than the first monomer solution.

The preparation of water-absorbing polymer beads is described in the monograph "Modern Superabsorbent Polymer Technology", F. L. Buchholz and A. T. Graham, Wiley-VCH, 1998, pages 71 to 103.

Being products which absorb aqueous solutions, water-absorbing polymers are used to produce diapers, tampons, sanitary napkins and other hygiene articles, but also as water-retaining agents in market gardening.

Spray polymerization allows the process steps of polymerization and drying to be combined. In addition, the bead size can be set within certain limits by virtue of suitable process control.

The preparation of water-absorbing polymer beads by polymerization of droplets of a monomer solution is described, for example, in EP 348 180 A1, JP 05/132503 A, WO 96/40427 A1, U.S. Pat. No. 5,269,980, DE 103 14 466 A1, DE 103 40 253 A1 and DE 10 2004 024 437 A1, WO 2006/077054 A1, and also the prior German application 102006001596.7 and the prior PCT application PCT/EP2006/062252.

JP 05/132503 A discloses a spray polymerization process by redox polymerization, wherein the components of the redox initiator are not mixed until beyond the nozzle.

WO 2006/077054 A1 describes a process in which use of surface-active crosslinkers generates a crosslinker gradient.

The prior PCT application PCT/EP2006/062252 describes a process wherein a concentration gradient is obtained in the droplets by means of a two-substance nozzle.

DE 10 2004 042 946 A1, DE 10 2004 042 948 A1 and DE 10 2004 042 955 A1, and also the prior German application 102005019398.6, describe the preparation of thickeners by spray polymerization.

It was an object of the present invention to provide an improved process for preparing water-absorbing polymer beads by polymerizing droplets of a monomer solution in a gas phase surrounding the droplets.

The object is achieved by a process for preparing water-absorbing polymer beads by polymerizing droplets comprising
a) at least one ethylenically unsaturated monomer,
b) at least one crosslinker,
c) at least one initiator,
d) water,
in a gas phase surrounding the droplets, the droplets being obtained by enveloping a first monomer solution with a second monomer solution, wherein the second monomer solution polymerizes to give a more highly crosslinked polymer than the first monomer solution.

By virtue of the second monomer solution polymerizing to give a more highly crosslinked polymer, water-absorbing polymer beads with a crosslinking gradient are obtained in one step. The higher crosslinking can be achieved, for example, by virtue of a higher crosslinker concentration and/or a more effective crosslinker in the second monomer solution.

The molar crosslinker concentration in the second monomer solution is typically at least 10%, preferably at least 20%, preferentially at least 50%, more preferably at least 100%, most preferably at least 200%, higher than in the first monomer solution.

The first monomer solution comprises preferably at least 0.2% by weight, preferentially at least 0.4% by weight, more preferably at least 0.6% by weight, most preferably at least 0.8% by weight, of crosslinker b), based in each case on monomer a).

The second monomer solution comprises preferably at least 0.6% by weight, preferentially at least 0.8% by weight, more preferably at least 1.5% by weight, most preferably at least 3.0% by weight, of crosslinker b), based in each case on monomer a).

In a preferred embodiment of the present invention, the second monomer solution is metered in through an annular gap surrounding the feed of the first monomer solution. The annular gap has a gap width of preferably from 25 µm to 250 µm, more preferably from 50 to 200 µm, most preferably from 100 to 150 µm.

The droplets obtained have a mean diameter of preferably at least 200 µm, more preferably of at least 250 µm, most preferably of at least 300 µm, the droplet diameter being determinable by light scattering.

The droplets are preferably monodisperse; more preferably, less than 10% by weight of the droplets have a diameter which deviates by more than 50% from the mean diameter.

The water-absorbing polymer beads obtainable by the process according to the invention have a permeability (SFC) of typically at least $10 \times 10^{-7}$ cm$^3$s/g, preferably at least $30 \times 10^{-7}$ cm$^3$s/g, preferentially at least $50 \times 10^{-7}$ cm$^3$s/g, more preferably at least $70 \times 10^{-7}$ cm$^3$s/g, most preferably at least $90 \times 10^{-7}$ cm$^3$s/g. The permeability (SFC) of the water-absorbing polymer beads is typically less than $250 \times 10^{-7}$ cm$^3$s/g.

The water-absorbing polymer beads obtainable by the process according to the invention have an absorbency under a load of 4.83 kPa (AUL0.7 psi) of typically at least 15 g/g, preferably of at least 20 g/g, preferentially at least 25 g/g, more preferably of at least 27 g/g, most preferably of at least 29 g/g. The absorbency under a load of 4.83 kPa (AUL0.7 psi) of the water-absorbing polymer beads is typically less than 50 g/g.

The water-absorbing polymer beads obtainable by the process according to the invention have a centrifuge retention capacity (CRC) of typically at least 20 g/g, preferably at least 25 g/g, preferentially at least 30 g/g, more preferably at least 32 g/g, most preferably at least 34 g/g. The centrifuge retention capacity (CRC) of the water-absorbing polymer beads is typically less than 50 g/g.

The water-absorbing polymer beads obtainable by the process according to the invention have a content of extractables of typically less than 15% by weight, preferably less than 10% by weight, preferentially less than 5% by weight, more preferably less than 4% by weight, most preferably less than 3% by weight.

The process according to the invention enables the preparation of water-absorbing polymer beads with very uniform crosslinking density at the bead surface.

In the measurement of the modulus of elasticity of the outer bead surface, typically less than 50%, preferably less than 40%, preferentially less than 30%, more preferably less than 25%, most preferably less than 20%, have a modulus of elasticity of less than 60% of the mean modulus of elasticity.

The water-absorbing polymer beads obtainable by the process according to the invention have a mean modulus of elasticity of the outer bead surface of typically at least 50 kPa, preferably at least 90 kPa, preferentially at least 120 kPa, more preferably at least 150 kPa, most preferably at least 180 kPa. The mean modulus of elasticity of the outer bead surface of the water-absorbing polymer beads is typically less than 500 kPa.

The mean diameter of the water-absorbing polymer beads obtainable by the process according to the invention is preferably at least 200 μm, more preferably from 250 to 600 μm, very particularly from 300 to 500 μm, the bead diameter being determinable by light scattering and meaning the volume-average mean diameter. 90% of the polymer beads have a diameter of preferably from 100 to 800 μm, more preferably from 150 to 700 μm, most preferably from 200 to 600 μm.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 50 g/100 g of water, and preferably have at least one acid group each.

Suitable monomers a) are, for example, ethylenically unsaturated carboxylic acids such as acrylic acid, methacrylic acid, maleic acid, fumaric acid and itaconic acid. Particularly preferred monomers are acrylic acid and methacrylic acid. Very particular preference is given to acrylic acid.

The preferred monomers a) have at least one acid group, the acid groups preferably being at least partly neutralized.

The proportion of acrylic acid and/or salts thereof in the total amount of monomers a) is preferably at least 50 mol %, more preferably at least 90 mol %, most preferably at least 95 mol %.

The acid groups of the monomers a) are typically partly neutralized, preferably to an extent of from 25 to 85 mol %, preferentially to an extent of from 50 to 80 mol %, more preferably from 60 to 75 mol %, for which the customary neutralizing agents can be used, preferably alkali metal hydroxides, alkali metal oxides, alkali metal carbonates or alkali metal hydrogencarbonates, and mixtures thereof. Instead of alkali metal salts, it is also possible to use ammonium salts. Sodium and potassium are particularly preferred as alkali metals, but very particular preference is given to sodium hydroxide, sodium carbonate or sodium hydrogencarbonate, and mixtures thereof. Typically, the neutralization is achieved by mixing in the neutralizing agent as an aqueous solution, as a melt or preferably also as a solid. For example, sodium hydroxide with a water content significantly below 50% by weight may be present as a waxy material having a melting point above 23° C. In this case, metered addition as piece material or melt at elevated temperature is possible.

The monomers a), especially acrylic acid, comprise preferably up to 0.025% by weight of a hydroquinone monoether. Preferred hydroquinone monoethers are hydroquinone monomethyl ether (MEHQ) and/or tocopherols.

Tocopherol is understood to mean compounds of the following formula

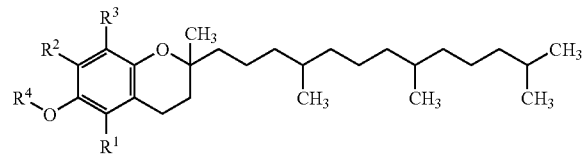

where $R^1$ is hydrogen or methyl, $R^2$ is hydrogen or methyl, $R^3$ is hydrogen or methyl, and $R^4$ is hydrogen or an acyl radical having from 1 to 20 carbon atoms.

Preferred radicals for $R^4$ are acetyl, ascorbyl, succinyl, nicotinyl and other physiologically compatible carboxylic acids. The carboxylic acids may be mono-, di- or tricarboxylic acids.

Preference is given to alpha-tocopherol where $R^1$=$R^2$=$R^3$=methyl, in particular racemic alpha-tocopherol. $R^1$ is more preferably hydrogen or acetyl. RRR-alpha-tocopherol is especially preferred.

The monomer solution comprises preferably at most 130 ppm by weight, more preferably at most 70 ppm by weight, preferably at least 10 ppm by weight, more preferably at least 30 ppm by weight, in particular around 50 ppm by weight, of hydroquinone monoether, based in each case on acrylic acid, acrylic acid salts also being considered as acrylic acid. For example, the monomer solution can be prepared by using acrylic acid having an appropriate content of hydroquinone monoether.

Crosslinkers b) are compounds having at least two free-radically polymerizable groups which can be polymerized by a free-radical mechanism into the polymer network. Suitable crosslinkers b) are, for example, ethylene glycol dimethacrylate, diethylene glycol diacrylate, allyl methacrylate, trimethylolpropane triacrylate, triallylamine, tetraallyloxyethane, as described in EP 530 438 A1, di- and triacrylates, as described in EP 547 847 A1, EP 559 476 A1, EP 632 068 A1, WO 93/21237 A1, WO 2003/104299 A1, WO 2003/104300 A1, WO 2003/104301 A1 and in DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/32962 A2.

Suitable crosslinkers b) are in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate or ethylene glycol dimethacrylate, and also trimethylolpropane triacrylate and allyl compounds such as allyl (meth)acrylate, triallyl cyanurate, diallyl maleate, polyallyl esters, tetraallyloxyethane, triallylamine, tetraallylethylenediamine, allyl esters of phosphoric acid and vinylphosphonic acid derivatives, as described, for example, in EP 343 427 A2. Further suitable crosslinkers b) are pentaerythritol diallyl ether, pentaerythritol triallyl ether and pentaerythritol tetraallyl ether, polyethylene glycol diallyl ether, ethylene glycol diallyl ether, glycerol diallyl ether and glycerol triallyl ether, polyallyl ethers based on sorbitol, and ethoxylated variants thereof. In the process according to the invention, it is possible to use di(meth)acrylates of polyethylene glycols, the polyethylene glycol used having a molecular weight between 300 and 1000.

However, particularly advantageous crosslinkers b) are di- and triacrylates of 3- to 20-tuply ethoxylated glycerol, of 3- to 20-tuply ethoxylated trimethylolpropane, of 3- to 20-tuply ethoxylated trimethylolethane, in particular di- and triacrylates of 2- to 6-tuply ethoxylated glycerol or of 2- to 6-tuply ethoxylated trimethylolpropane, of 3-tuply propoxylated glycerol or of 3-tuply propoxylated trimethylolpropane, and also of 3-tuply mixed ethoxylated or propoxylated glycerol or of 3-tuply mixed ethoxylated or propoxylated trimethylolpropane, of 15-tuply ethoxylated glycerol or of 15-tuply ethoxylated trimethylolpropane, and also of 40-tuply ethoxylated glycerol, of 40-tuply ethoxylated trimethylolethane or of 40-tuply ethoxylated trimethylolpropane.

Very particularly preferred crosslinkers b) are the polyethoxylated and/or -propoxylated glycerols which have been esterified with acrylic acid or methacrylic acid to give di- or triacrylates, as described, for example in WO 2003/104301 A1. Di- and/or triacrylates of 3- to 10-tuply ethoxylated glycerol are particularly advantageous.

Very particular preference is given to di- or triacrylates of 1- to 5-tuply ethoxylated and/or propoxylated glycerol. Most preferred are the triacrylates of 3- to 5-tuply ethoxylated and/or propoxylated glycerol.

The initiators c) used may be all compounds which disintegrate into free radicals under the polymerization conditions, for example peroxides, hydroperoxides, hydrogen peroxide, persulfates, azo compounds and redox initiators. Preference is given to the use of water-soluble initiators. In some cases, it is advantageous to use mixtures of various initiators, for example mixtures of hydrogen peroxide and sodium or potassium peroxodisulfate. Mixtures of hydrogen peroxide and sodium peroxodisulfate can be used in any proportion.

Particularly preferred initiators c) are azo initiators such as 2,2'-azobis[2-(2-imidazolin-2-yl)propane]dihydrochloride and 2,2'-azobis[2-(5-methyl-2-imidazolin-2-yl)propane]dihydrochloride, and photoinitiators such as 2-hydroxy-2-methylpropiophenone and 1-[4-(2-hydroxyethoxy)phenyl]-2-hydroxy-2-methyl-1-propan-1-one, redox initiators such as sodium persulfate/hydroxymethylsulfinic acid, ammonium peroxodisulfate/hydroxy-methylsulfinic acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2-hydroxyethoxy)phenyl]-2-hydroxy-2-methyl-1-propan-1-one, and mixtures thereof.

The initiators are used in customary amounts, for example in amounts of from 0.001 to 5% by weight, preferably from 0.01 to 1% by weight, based on the monomers a).

For optimal action, the preferred polymerization inhibitors require dissolved oxygen. Therefore, the monomer solution can be freed of dissolved oxygen before the polymerization by inertization, i.e. flowing through with an inert gas, preferably nitrogen. The oxygen content of the monomer solution is preferably lowered before the polymerization to less than 1 ppm by weight, more preferably to less than 0.5 ppm by weight.

The polymerization inhibitors can also be removed by absorption, for example on activated carbon.

The solids content of the monomer solution is preferably at least 35% by weight, preferably at least 38% by weight, more preferably at least 40% by weight, most preferably at least 42% by weight. The solids content is the sum of all constituents which are involatile after the polymerization. These are monomer a), crosslinker b) and initiator c).

The monomer solution is dropletized for polymerization in the gas phase. The oxygen content of the gas phase is preferably from 0.001 to 0.15% by volume, more preferably from 0.002 to 0.1% by volume, most preferably from 0.005 to 0.05% by volume.

As well as oxygen, the gas phase preferably comprises only inert gases, i.e. gases which, under reaction conditions, do not intervene in the polymerization, for example nitrogen and/or steam.

The dropletization involves metering a monomer solution into the gas phase to form droplets. The dropletization of the monomer solution can be carried out, for example, by means of a dropletizer plate.

A dropletizer plate is a plate having at least one bore, the liquid entering the bore from the top. The dropletizer plate or the liquid can be oscillated, which generates a chain of ideally monodisperse droplets at each bore on the underside of the dropletizer plate. In a preferred embodiment, the dropletizer plate is not agitated.

The number and size of the bores are selected according to the desired capacity and droplet size. The droplet diameter is typically 1.9 times the diameter of the bore. What is important here is that the liquid to be dropletized does not pass through the bore too rapidly and the pressure drop over the bore is not too great. Otherwise, the liquid is not dropletized, but rather the liquid jet is broken up (sprayed) owing to the high kinetic energy. The dropletizer is operated in the flow range of laminar jet decomposition, i.e. the Reynolds number based on the throughput per bore and the bore diameter is preferably less than 2000, preferentially less than 1000, more preferably less than 500 and most preferably less than 100. The pressure drop through the bore is preferably less than 2.5 bar, more preferably less than 1.5 bar and most preferably less than 1 bar.

The dropletizer plate has typically at least one bore, preferably at least 10, more preferably at least 50 and typically up to 10 000 bores, preferably up to 5000, more preferably up to 1000 bores, the bores typically being distributed uniformly over the dropletizer plate, preferably in so-called triangular pitch, i.e. three bores in each case form the corners of an equilateral triangle. The diameter of the bores is adjusted to the desired droplet size.

However, the dropletization can also be carried out by means of pneumatic drawing dies, rotation, cutting of a jet or rapidly actuable microvalve dies.

In a pneumatic drawing die, a liquid jet together with a gas stream is accelerated through a diaphragm. The gas rate can be used to influence the diameter of the liquid jet and hence the droplet diameter.

In the case of dropletization by rotation, the liquid passes through the orifices of a rotating disk. As a result of the centrifugal force acting on the liquid, droplets of defined size are torn off. Preferred apparatus for rotary dropletization are described, for example, in DE 43 08 842 A1.

The emerging liquid jet can also be cut into defined segments by means of a rotating blade. Each segment then forms a droplet.

In the case of use of microvalve dies, droplets with defined liquid volume are generated directly.

The gas phase preferably flows as carrier gas through the reaction chamber. The carrier gas can be conducted through the reaction chamber in cocurrent or in countercurrent to the free-falling droplets of the monomer solution, preferably in cocurrent. After one pass, the carrier gas is preferably recycled at least partly, preferably to an extent of at least 50%, more preferably to an extent of at least 75%, into the reaction chamber as cycle gas. Typically, a portion of the carrier gas is discharged after each pass, preferably up to 10%, more preferably up to 3% and most preferably up to 1%.

The polymerization is preferably carried out in a laminar gas flow. A laminar gas flow is a gas flow in which the individual layers of the flow do not mix but rather move in parallel. A measure of the flow conditions is the Reynolds number (Re). Below a critical Reynolds number ($Re_{crit}$) of 2300, the gas flow is laminar. The Reynolds number of the laminar gas flow is preferably less than 2000, more preferably less than 1500 and most preferably less than 1000. The lower limiting case of the laminar inert gas flow is a standing inert gas atmosphere (Re=0), i.e. inert gas is not fed in continuously.

The gas velocity is preferably adjusted such that the flow in the reactor is directed, for example no convection currents opposed to the general flow direction are present, and is, for example, from 0.01 to 5 m/s, preferably from 0.02 to 4 m/s, more preferably from 0.05 to 3 m/s, most preferably from 0.1 to 2 m/s.

The carrier gas is appropriately preheated to the reaction temperature upstream of the reactor.

The reaction temperature in the thermally induced polymerization is preferably from 70 to 250° C., more preferably from 100 to 220° C. and most preferably from 120 to 200° C.

The reaction can be carried out under elevated pressure or under reduced pressure; preference is given to a reduced pressure of up to 100 mbar relative to ambient pressure.

The reaction offgas, i.e. the carrier gas leaving the reaction chamber, may, for example, be cooled in a heat exchanger. This condenses water and unconverted monomer a). The reaction offgas can then be reheated at least partly and recycled into the reactor as cycle gas. A portion of the reaction offgas can be discharged and replaced by fresh carrier gas, in which case water and unconverted monomers a) present in the reaction offgas can be removed and recycled.

Particular preference is given to a thermally integrated system, i.e. a portion of the waste heat in the cooling of the offgas is used to heat the cycle gas.

The reactors can be trace-heated. In this case, the trace heating is adjusted such that the wall temperature is at least 5° C. above the internal reactor temperature and condensation on the reactor walls is reliably prevented.

The reaction product can be withdrawn from the reactor in a customary manner, preferably at the bottom by means of a conveying screw, and, if appropriate, dried down to the desired residual moisture content and to the desired residual monomer content.

The polymer beads can subsequently be postcrosslinked for further improvement of the properties.

Postcrosslinkers are compounds which comprise at least two groups which can form covalent bonds with the carboxylate groups of the hydrogel. Suitable compounds are, for example, alkoxysilyl compounds, polyaziridines, polyamines, polyamidoamines, di- or polyepoxides, as described in EP 83 022 A2, EP 543 303 A1 and EP 937 736 A2, di- or polyfunctional alcohols as described in DE 33 14 019 A1, DE 35 23 617 A1 and EP 450 922 A2, or β-hydroxyalkylamides, as described in DE 102 04 938 A1 and U.S. Pat. No. 6,239,230.

In addition, DE 40 20 780 C1 describes cyclic carbonates, DE 198 07 502 A1 describes 2-oxazolidone and its derivatives such as 2-hydroxyethyl-2-oxazolidone, DE 198 07 992 C1 describes bis- and poly-2-oxazolidinones, DE 198 54 573 A1 describes 2-oxotetrahydro-1,3-oxazine and its derivatives, DE 198 54 574 A1 describes N-acyl-2-oxazolidones, DE 102 04 937 A1 describes cyclic ureas, DE 103 34 584 A1 describes bicyclic amide acetals, EP 1 199 327 A2 describes oxetanes and cyclic ureas, and WO 2003/31482 A1 describes morpholine-2,3-dione and its derivatives, as suitable postcrosslinkers.

The amount of postcrosslinker is preferably from 0.01 to 1% by weight, more preferably from 0.05 to 0.5% by weight, most preferably from 0.1 to 0.2% by weight, based in each case on the polymer.

The postcrosslinking is typically performed in such a way that a solution of the postcrosslinker is sprayed onto the hydrogel or the dry polymer beads. The spraying is followed by thermal drying, and the postcrosslinking reaction can take place either before or during the drying.

The spraying of a solution of the crosslinker is preferably performed in mixers with moving mixing tools, such as screw mixers, paddle mixers, disk mixers, plowshare mixers and shovel mixers. Particular preference is given to vertical mixers, very particular preference to plowshare mixers and shovel mixers. Suitable mixers are, for example, Lödige mixers, Bepex mixers, Nauta mixers, Processall mixers and Schugi mixers.

The thermal drying is preferably carried out in contact dryers, more preferably paddle dryers, most preferably disk dryers. Suitable dryers are, for example, Bepex dryers and Nara dryers. Moreover, it is also possible to use fluidized bed dryers.

The drying can be effected in the mixer itself, by heating the jacket or blowing in warm air. Equally suitable is a downstream dryer, for example a staged dryer, a rotary tube oven or a heatable screw. It is particularly advantageous to mix and dry in a fluidized bed dryer.

Preferred drying temperatures are in the range from 170 to 250° C., preferably from 180 to 220° C. and more preferably from 190 to 210° C. The preferred residence time at this temperature in the reaction mixer or dryer is preferably at least 10 minutes, more preferably at least 20 minutes, most preferably at least 30 minutes.

The process according to the invention enables the preparation of water-absorbing polymer beads with a high centrifuge retention capacity (CRC), a high absorbency under a load of 4.83 kPa (AUL0.7 psi), a high permeability (SFC) and a low level of extractables.

The present invention further provides water-absorbing polymer beads which are obtainable by the process according to the invention.

The present invention further provides water-absorbing polymer beads which have a centrifuge retention capacity (CRC) of at least 30 g/g and a permeability (SFC) of at least $30 \times 10^{-7}$ cm$^3$s/g, and less than 30% of the measured moduli of elasticity of the outer bead surface have a value of less than 60% of the mean modulus of elasticity.

The water-absorbing polymer beads obtainable by the process according to the invention typically have the shape of hollow spheres. The present invention therefore further provides water-absorbing polymer beads comprising at least one cavity in the bead interior.

The ratio of maximum diameter of the cavity to maximum diameter of the polymer bead is preferably at least 0.1, more preferably at least 0.3, most preferably at least 0.4.

The quotient of mean modulus of elasticity of the outer bead surface and mean modulus of elasticity of the inner wall of the cavity is preferably at least 2.5, more preferably at least 2.8, most preferably at least 3.

The inventive water-absorbing polymer beads are approximately round, i.e. the polymer beads have a mean sphericity of typically at least 0.84, preferably at least 0.86, more preferably at least 0.88 and most preferably at least 0.9. The sphericity (SPHT) is defined as $$SPHT = \frac{4\pi A}{U}$$

where A is the cross-sectional area and U is the cross-sectional circumference of the polymer beads. The mean sphericity is the volume-average sphericity.

The mean sphericity can be determined, for example, with the Camsizer® image analysis system (Retsch Technolgy GmbH; Germany):

For the measurement, the product is introduced through a funnel and conveyed to the falling shaft with a metering channel. While the beads fall past a light wall, they are recorded selectively by a camera. The images recorded are evaluated by the software in accordance with the parameters selected.

To characterize the roundness, the parameter designated as sphericity in the program is employed. The parameters reported are the mean volume-weighted sphericities, the volume of the beads being determined via the equivalent diameter $xc_{min}$. To determine the equivalent diameter $xc_{min}$, the longest chord diameter for a total of 32 different spatial directions is measured in each case. The equivalent diameter $xc_{min}$ is the shortest of these 32 chord diameters. The equivalent diameter $xc_{min}$ corresponds to the mesh size of a screen that the bead can just pass through. To record the beads, the so-called CCD-zoom camera (CAM-Z) is used. To control the metering channel, a surface coverage fraction of 0.5% is predefined.

Polymer beads with relatively low sphericity are obtained by reverse suspension polymerization when the polymer beads are agglomerated during or after the polymerization.

The water-absorbing polymer beads prepared by customary solution polymerization (gel polymerization) are ground and classified after drying to obtain irregular polymer beads. The mean sphericity of these polymer beads is between approx. 0.72 and approx. 0.78.

The present invention further provides processes for preparing hygiene articles, especially diapers, comprising the use of water-absorbing polymer beads prepared by the above-mentioned process.

The present invention further provides for the use of inventive water-absorbing polymer beads in hygiene articles, for thickening wastes, especially medical wastes, or as a water-retaining agent in agriculture.

The water-absorbing polymer beads are tested by means of the test methods described below.

Methods:

The measurements should, unless stated otherwise, be carried out at an ambient temperature of 23±2° C. and a relative air humidity of 50±10%. The water-absorbing polymers are mixed thoroughly before the measurement.

Saline Flow Conductivity (SFC)

The saline flow conductivity of a swollen gel layer under a load of 0.3 psi (2070 Pa) is, as described in EP 640 330 A1, determined as the gel layer permeability of a swollen gel layer of water-absorbing polymer beads, except that the apparatus described on page 19 and in FIG. 8 in the aforementioned patent application was modified to the effect that the glass frit (40) is no longer used, the plunger (39) consists of the same polymer material as the cylinder (37) and now comprises 21 bores of equal size distributed uniformly over the entire contact surface. The procedure and evaluation of the measurement remain unchanged from EP 640 330 A1. The flow rate is recorded automatically.

The saline flow conductivity (SFC) is calculated as follows:

SFC[cm$^3$s/g]=$(Fg(t=0) \times L0)/(d \times A \times WP)$, where Fg(t=0) is the flow rate of NaCl solution in g/s, which is obtained by means of a linear regression analysis of the Fg(t) data of the flow determinations by extrapolation to t=0, L0 is the thickness of the gel layer in cm, d is the density of the NaCl solution in g/cm$^3$, A is the surface area of the gel layer in cm$^2$, and WP is the hydrostatic pressure over the gel layer in dyn/cm$^2$.

Mean Modulus of Elasticity

To determine the mean modulus of elasticity (Young's modulus of elasticity), the water-absorbing polymer beads are swollen in excess 0.9% by weight sodium chloride solution for 30 min. A glass micropipette having an internal diameter D of 50 μm is placed onto the bead surface to be examined. Subsequently, a reduced pressure is generated in the micropipette, such that the surface of the water-absorbing polymer bead to be examined is sucked into the micropipette. The length L is the maximum length by which the bead surface is sucked into the micropipette. The reduced pressure is selected such that the bead surface sucked in has the shape of a meniscus and the length L is between 5 and 10 μm. The length L and the accompanying pressure difference Δp measured relative to the surrounding solution in the micropipette are noted. Lengths L which are too small reduce the accuracy of the measurement; at excess lengths L, the linear measurement range is departed from, i.e. the length L is no longer proportional to the pressure difference Δp. The fact that the linear range has been departed from can also be recognized in that the bead surface sucked in adjoins the inner wall of the micropipette.

The diameter of the swollen polymer beads should be at least 250 μm. When the bead diameters are too low, even the curvature of the polymer bead simulates a meniscus in the micropipette. To analyze smaller water-absorbing polymer beads, it is therefore necessary to use micropipettes having a smaller internal diameter, in which case the range for the length L should also be adjusted.

The mean modulus of elasticity is calculated according to $$E = \frac{3}{4\pi} \cdot \Delta p \cdot \frac{D}{L}.$$

The measurement is repeated at least 20 times. The arithmetic mean of the values obtained is the mean modulus of elasticity.

The deformation of the water-absorbing polymer beads during the measurement can be recorded by means of a digital imaging system and evaluated by computer.

FIG. 1 shows an example of a test setup on a microscope slide. In this figure, the reference numerals have the following meanings:

1 to image evaluation
2 to pressure measurement
3 to pressure generation
4 solution
5 polymer bead When water-absorbing polymer beads which have the shape of hollow spheres are examined, it is also possible to measure the modulus of elasticity of the inner wall of the cavity. To this end, the swollen water-absorbing polymer beads are cut through by means of a scalpel.

Centrifuge Retention Capacity (CRC)

The centrifuge retention capacity of the water-absorbing polymer beads is determined by the EDANA (European Disposables and Nonwovens Association) recommended test method No. 441.2-02 "Centrifuge retention capacity".

Absorbency Under Load (AUL0.7 psi)

The absorbency under load of the water-absorbing polymer beads is determined by the EDANA (European Disposables and Nonwovens Association) recommended test method No. 442.2-02 "Absorption under pressure", using a weight of 49 g/cm$^2$ (0.7 psi) instead of a weight of 21 g/cm$^2$ (0.3 psi).

Extractables

The content of extractables of the water-absorbing polymer beads is determined by the EDANA (European Disposables and Nonwovens Association) recommended test method No. 470.2-02 "Extractable".

The EDANA test methods are obtainable, for example, from the European Disposables and Nonwovens Association, Avenue Eugene Plasky 157, B-1030 Brussels, Belgium.

EXAMPLES

Example 1 (Comparative Example)

14.3 kg of sodium acrylate (37.5% by weight solution in water), 1.4 kg of acrylic acid and 350 g of water were mixed with 22 g of 15-tuply ethoxylated trimethylolpropane triacrylate. The solution was dropletized into a heated dropletizer tower filled with a nitrogen atmosphere (180° C., height 12 m, width 2 m, gas velocity 0.1 m/s in cocurrent). The metering rate was 16 kg/h. The dropletizer plate had 30×200 μm bores. Just upstream of the dropletizer, the initiator was metered into the monomer solution by means of a static mixer. The initiator used was a 3% by weight solution of 2,2'-azobis[2-(2-imidazolin-2-yl)propane]dihydrochloride in water. The metering rate of the initiator solution was 1.1 kg/h.

The water-absorbing polymer beads had the following properties:

| | |
|---|---|
| CRC | 34.5 g/g |
| AUL0.7 psi | 16.2 g/g |
| Extractables | 4.0% by weight |
| SFC | $0.9 \times 10^{-7}$ cm$^3$s/g |

The mean modulus of elasticity of the outer bead surface was 60 kPa, the mean modulus of elasticity of the inner wall of the cavity was 30 kPa and the quotient of the mean moduli of elasticity was 2.

The mean modulus of elasticity is the mean value from 20 individual measurements. A total of 4 individual measurements of the modulus of elasticity of the outer bead surface gave a value of less than 36 kPa.

The mean bead diameter was 350 μm.

Example 2 (Comparative Example)

The water-absorbing polymer beads from example 1 were sprayed with a solution of 0.08% by weight of ethylene glycol diglycidyl ether, 1.75% by weight of water and 1.17% by weight of propylene glycol, based in each case on the water-absorbing polymer beads, and dried at 120° C. in a forced-air drying cabinet for 30 minutes.

The water-absorbing polymer beads had the following properties:

| | |
|---|---|
| CRC | 34.8 g/g |
| AUL0.7 psi | 27.2 g/g |
| Extractables | 2.9% by weight |
| SFC | $16 \times 10^{-7}$ cm$^3$s/g |

The mean modulus of elasticity of the outer bead surface was 150 kPa, the mean modulus of elasticity of the inner wall of the cavity was 40 kPa and the quotient of the mean moduli of elasticity was 3.75.

The mean modulus of elasticity is the mean value from 20 individual measurements. A total of 10 individual measurements of the modulus of elasticity of the outer bead surface gave a value of less than 90 kPa.

The mean bead diameter was 350 μm.

Example 3

14.3 kg of sodium acrylate (37.5% by weight solution in water), 1.4 kg of acrylic acid and 350 g of water were mixed with 22 g of 15-tuply ethoxylated trimethylolpropane triacrylate (first monomer solution). 14.3 kg of sodium acrylate (37.5% by weight solution in water), 1.4 kg of acrylic acid and 350 g of water were mixed with 44 g of 15-tuply ethoxylated trimethylolpropane triacrylate (second monomer solution). The solutions were dropletized into a heated dropletizer tower filled with nitrogen atmosphere (180° C., height 12 m, width 2 m, gas velocity 0.1 m/s in cocurrent). The metering rate of the first monomer solution was 16 kg/h. The metering rate of the second monomer solution was 1.6 kg/h. The dropletizer plate had 30×200 μm bores, and each bore was surrounded by an annular gap. Just upstream of the dropletizer, the initiator was metered into the monomer solutions by means of static mixers. The initiator used was a 3% by weight solution of 2,2'-azobis[2-(2-imidazolin-2-yl)propane]dihydrochloride in water. The metering rate of the initiator solution into the first monomer solution was 1.1 kg/h. The metering rate of the initiator solution into the second monomer solution was 0.1 kg/h.

The water-absorbing polymer beads had the following properties:

| | |
|---|---|
| CRC | 34.5 g/g |
| AUL0.7 psi | 22.1 g/g |
| Extractables | 3.5% by weight |
| SFC | $30 \times 10^{-7}$ cm$^3$s/g |

The mean modulus of elasticity of the outer bead surface was 90 kPa, the mean modulus of elasticity of the inner wall of the cavity was 40 kPa and the quotient of the mean moduli of elasticity was 2.25.

The mean modulus of elasticity is the mean value from 20 individual measurements. A total of 3 individual measurements of the modulus of elasticity of the outer bead surface gave a value of less than 54 kPa.

The mean bead diameter was 360 μm.

Example 4

The procedure of example 3 was repeated. The second monomer solution was prepared by using 88 g of 15-tuply ethoxylated trimethylolpropane triacrylate.

The water-absorbing polymer beads had the following properties:

| | |
|---|---|
| CRC | 34.9 g/g |
| AUL0.7 psi | 27.9 g/g |
| Extractables | 3.5% by weight |
| SFC | $50 \times 10^{-7}$ cm$^3$s/g |

The mean modulus of elasticity of the outer bead surface was 140 kPa, the mean modulus of elasticity of the inner wall of the cavity was 50 kPa and the quotient of the mean moduli of elasticity was 2.8.

The mean modulus of elasticity is the mean value from 20 individual measurements. A total of 4 individual measurements of the modulus of elasticity of the outer bead surface gave a value of less than 84 kPa.

The mean bead diameter was 370 µm.

Example 5

The procedure of example 3 was repeated. The second monomer solution was prepared by using 176 g of 15-tuply ethoxylated trimethylolpropane triacrylate.

The water-absorbing polymer beads had the following properties:

| | |
|---|---|
| CRC | 34.0 g/g |
| AUL0.7 psi | 29.3 g/g |
| Extractables | 3.0% by weight |
| SFC | $90 \times 10^{-7}$ cm$^3$s/g |

The mean modulus of elasticity of the outer bead surface was 180 kPa, the mean modulus of elasticity of the inner wall of the cavity was 60 kPa and the quotient of the mean moduli of elasticity was 3.

The mean modulus of elasticity is the mean value from 20 individual measurements. A total of 5 individual measurements of the modulus of elasticity of the outer bead surface gave a value of less than 108 kPa.

The mean bead diameter was 380 µm.

Example 6 (Comparative Example)

The procedure of example 6 of WO 2006/077054 A1 was repeated.

The water-absorbing polymer beads had the following properties:

| | |
|---|---|
| CRC | 21.2 g/g |
| AUL0.3 psi | 17.6 g/g |
| Extractables | 17.5% by weight |
| SFC | $12 \times 10^{-7}$ cm$^3$s/g |

The mean modulus of elasticity of the outer bead surface was 80 kPa, the mean modulus of elasticity of the inner wall of the cavity was 40 kPa and the quotient of the mean moduli of elasticity was 2.

The mean modulus of elasticity is the mean value from 20 individual measurements. A total of 4 individual measurements of the modulus of elasticity of the outer bead surface gave a value of less than 48 kPa.

The mean bead diameter was 210 µm.

Example 7 (Comparative Example)

14.275 kg of sodium acrylate (37.5% by weight solution in water) and 1.367 kg of acrylic acid were mixed with 0.358 kg of water, 22 g of 15-tuply ethoxylated trimethylolpropane triacrylate and 80 g of EDTA (10% by weight solution of the sodium salt of ethylenediaminetetraacetic acid in water). After addition of 33 g of 2,2'-azobis[2-(2-imidazolin-2-yl)propane]dihydrochloride (3% by weight solution in water) and 110 g of hydrogen peroxide (3% by weight solution in water), the solution was dropletized into a heated dropletization tower filled with nitrogen atmosphere (180° C., height 12 m, width 2 m, gas velocity 0.1 m/s in cocurrent). The metering rate was 16 kg/h. The dropletizer plate had 37×170 µm bores. The diameter of the dropletizer plate was 65 mm. Just upstream of the dropletizer, the initiator was mixed with the monomer solution by means of a static mixer.

The water-absorbing polymer beads had the following properties:

| | |
|---|---|
| CRC | 33.0 g/g |
| AUL0.7 psi | 25.0 g/g |
| Extractables | 7.0% by weight |
| SFC | $10 \times 10^{-7}$ cm$^3$s/g |

The mean modulus of elasticity of the outer bead surface was 90 kPa, the mean modulus of elasticity of the inner wall of the cavity was 40 kPa and the quotient of the mean moduli of elasticity was 2.25.

The mean modulus of elasticity is the mean value from 20 individual measurements. A total of 3 individual measurements of the modulus of elasticity of the outer bead surface gave a value of less than 54 kPa.

The mean bead diameter was 360 µm.

The invention claimed is:

1. A process for preparing water-absorbing polymer beads comprising
    (a) providing a first monomer solution comprising
        (i) at least one ethylenically unsaturated monomer,
        (ii) at least one crosslinker,
        (iii) at least one initiator, and
        (iv) water;
    (b) providing a second monomer solution comprising
        (i) at least one ethylenically unsaturated monomer,
        (ii) at least one crosslinker,
        (iii) at least one initiator, and
        (iv) water, and
        having a molar crosslinker concentration at least 10% higher than in the first monomer solution;
    (c) forming droplets in a surrounding gas phase, the droplets obtained by enveloping the first monomer solution with the second monomer solution by metering the first monomer solution into the gas phase through at least one bore and a pressure drop through the bore is less than 2.5 bar, and metering the second monomer solution in through an annular gap which surrounds a feed of the first monomer solution; and
    (d) polymerizing the droplets formed in (c) in the surrounding gas phase to provide water-absorbing polymer beads having a crosslinking gradient wherein the enveloping second monomer solution polymerizes to give a more highly crosslinked polymer than the polymerized enveloped first polymer solution.

2. The process according to claim 1, wherein a molar crosslinker concentration in the second monomer solution is at least 20% higher than in the first monomer solution.

3. The process according to claim 1, wherein the annular gap has a width of at least 50 µm.

4. The process according to claim 1, wherein the droplets have a mean diameter of at least 200 µm.

5. The process according to claim 1, wherein the monomer a) has at least one acid group.

6. The process according to claim 5, wherein the acid groups of the monomer a) have been at least partly neutralized.

7. The process according to claim 1, wherein the monomer a) is acrylic acid to an extent of at least 50 mol %.

8. The process according to claim 1, wherein the resulting polymer beads are dried and/or postcrosslinked in at least one further process step.

\* \* \* \* \*